(12) United States Patent
Ito

(10) Patent No.: US 9,488,553 B2
(45) Date of Patent: Nov. 8, 2016

(54) TISSUE PIECE TREATING APPARATUS AND METHOD OF OPERATING TISSUE PIECE TREATING APPARATUS

(71) Applicants: Sakura Seiki Co., Ltd., Chikuma-shi, Nagano (JP); Sakura Finetek Japan Co., Ltd., Chuo-ku, Tokyo (JP)

(72) Inventor: Atsuo Ito, Chikuma (JP)

(73) Assignees: Sakura Seiki Co., Ltd., Nagano (JP); Sakura Finetek Japan Co., Ltd., Tokyo (JP)

( * ) Notice: Subject to any disclaimer, the term of this patent is extended or adjusted under 35 U.S.C. 154(b) by 0 days.

(21) Appl. No.: 14/894,952

(22) PCT Filed: May 16, 2014

(86) PCT No.: PCT/JP2014/063124
§ 371 (c)(1),
(2) Date: Nov. 30, 2015

(87) PCT Pub. No.: WO2014/203662
PCT Pub. Date: Dec. 24, 2014

(65) Prior Publication Data
US 2016/0116382 A1 Apr. 28, 2016

(30) Foreign Application Priority Data
Jun. 18, 2013 (JP) .................................. 2013-127949

(51) Int. Cl.
*A61B 10/00* (2006.01)
*G01N 1/31* (2006.01)
*G01N 1/36* (2006.01)

(52) U.S. Cl.
CPC . *G01N 1/31* (2013.01); *G01N 1/36* (2013.01)

(58) Field of Classification Search
CPC ................................. G01N 1/31; A61B 10/00
See application file for complete search history.

(56) References Cited

FOREIGN PATENT DOCUMENTS

| JP | 7278524 | 10/1995 |
|---|---|---|
| JP | 2009281745 | 12/2009 |
| JP | 2010078471 | 4/2010 |

OTHER PUBLICATIONS

Sakura Seiki Co., Ltd., et al., International search report for PCT/JP2014/063124 (Aug. 19, 2014).

*Primary Examiner* — Jyoti Nagpaul
(74) *Attorney, Agent, or Firm* — Blakely Sokoloff Taylor & Zafman LLP

(57) ABSTRACT

The present invention addresses the problem of providing a technology capable of automatically preparing a mixed liquid having a fixed ratio. To address the problem, the following processes are carried out in a tissue piece treating apparatus (10). (a) By use of a detection sensor (36), a dehydrating agent is transferred from a dehydrating agent tank (large-capacity tank (15)) to a treatment tank (11) until reaching a prescribed level. (b) By use of the detection sensor (36), an intermediate agent is transferred from an intermediate agent tank (large-capacity tank (17)) to the treatment tank (11) until reaching a prescribed level. (c) An admixture obtained by mixing the dehydrating agent by the process of (a) and the intermediate agent by the process of (b) is transferred from the treatment tank (11) to an admixture tank (14).

5 Claims, 6 Drawing Sheets

TISSUE PIECE TREATING APPARATUS AND METHOD OF OPERATING TISSUE PIECE TREATING APPARATUS

CROSS-REFERENCE TO RELATED APPLICATION

This is a 371 application claiming the benefit of International Patent Application No. PCT/JP2014/063124, filed May 16, 2014.

TECHNICAL FIELD

The present invention relates to a technique effectively applied to a tissue piece treating apparatus which supplies/drains different kinds of liquid chemical having different concentrations to/from a treatment tank containing a tissue piece in a predetermined order to apply an immersion treatment to the tissue piece, and effectively applied to a method of operating the tissue piece treating apparatus.

BACKGROUND ART

As a pretreatment for microscope observation of a tissue piece collected from a living thing (also called a specimen), there is used a sample preparation method of applying a fixing treatment, a dehydrating treatment, a degreasing treatment, a penetration (embedding) treatment to the tissue piece in this order. This sample preparation method is performed by immersing the tissue piece into various kinds of liquid chemical. For example, as liquid chemicals, formalin (fixing agent) is used in the fixing treatment, alcohol (dehydrating agent) is used in the dehydrating treatment, xylene (intermediate agent or degreasing agent) is used in the degreasing treatment, and paraffin (embedding agent) is used in the penetration treatment.

Japanese Patent Laid-Open No. 2009-281745 (PTL 1) describes a tissue piece treating apparatus capable of continuing treatment operation by replenishing a liquid chemical even if the liquid chemical supplied to a treatment tank runs short.

Further, Japanese Patent Laid-Open No. 2010-78471 (PTL 2) describes a tissue piece treating apparatus capable of reusing a liquid chemical which becomes unable to apply treatment to a tissue piece, as a cleaning liquid.

CITATION LIST

Patent Literature

PTL 1: Japanese Patent Laid-Open No. 2009-281745
PTL 2: Japanese Patent Laid-Open No. 2010-78471

SUMMARY OF INVENTION

Technical Problem

Meanwhile, even when the sample preparation method is used, for the case that the tissue piece contains a large amount of grease, for example, frequently water content and oil content are mixed in a deep part of the tissue piece, and sometimes the paraffin penetration becomes insufficient because of insufficient degreasing. As a countermeasure, sometimes a treatment by a mixed liquid (admixture) of xylene and alcohol is performed between the dehydrating treatment by alcohol and the degreasing treatment by xylene. By the use of this xylene-alcohol mixed liquid, the xylene-alcohol mixed liquid would penetrate into a deep part of the tissue piece to perform the dehydration and degreasing by a synergistic effect of dilution dehydration and grease dissolution.

When a worker (e.g., specimen engineer) himself or herself tries to mix xylene and alcohol in predetermined amounts to prepare a liquid chemical (mixed liquid), however, it takes time and labor and causes a problem of a dirty hand, a stinking room, a liquid chemical spilled over a floor, or the like.

Further, in the tissue piece treating apparatuses described in PTLs 1 and 2, liquid chemicals such as alcohol, xylene, and paraffin are stored in liquid chemical tanks separately, and supplied from the liquid chemical tanks to a treatment tank when target treatments are performed. That is, these tissue piece treating apparatuses do not handle the xylene-alcohol mixed liquid. Accordingly, the preparation of the xylene-alcohol mixed liquid is desired not to be performed by a worker but to be performed automatically by the tissue piece treating apparatus.

Note that, although, since each of the tissue piece treating apparatuses described in PTLs 1 and 2 supplies/drains alcohol and xylene to/from the same treatment tank, the alcohol remaining in the treatment tank is contained slightly in the xylene, for example, this does not provide the above synergetic effect of the xylene-alcohol mixed liquid.

An object of the present invention is to provide a tissue piece treating apparatus capable of preparing a mixed liquid having a certain ratio. The above and the other objects and novel features of the present invention will become clear from the description of the present specification and the attached drawings.

Solution to Problem

There will be explained briefly an outline of representative one of inventions disclosed in the present application, as follows.

A tissue piece treating apparatus in one embodiment of the present invention includes: a treatment tank to contain a tissue piece; a plurality of liquid chemical tanks that is connected communicatably to the treatment tank and stores liquid chemicals; a pump that depressurizes an inside of the treatment tank when a liquid chemical is transferred from the liquid chemical tank communicating with the treatment tank to the treatment tank, and pressurizes the inside of the treatment tank when a liquid chemical is transferred from the treatment tank to the liquid chemical tank communicating with the treatment tank; a detection sensor to detect that a predetermined amount of liquid chemical has been transferred to the treatment tank; and a control unit that is connected to the pump and the detection sensor via respective wirings and carries out a plurality of processes, the plurality of processes including the processes of (a) transferring a dehydrating agent from the liquid chemical tank storing the dehydrating agent to the treatment tank until the dehydrating agent reaches a predetermined amount by use of the detection sensor, (b) transferring an intermediate agent from the liquid chemical tank storing the intermediate agent to the treatment tank until the intermediate agent reaches a predetermined amount by use of the detection sensor, and (c) transferring an admixture obtained by mixing the dehydrating agent by the process (a) and the intermediate agent by the process (b) from the treatment tank to the liquid chemical tank in which the admixture is stored.

Further, a method of operating a tissue piece treating apparatus in one embodiment of the present invention is a method of operating a tissue piece treating apparatus including a treatment tank to contain a tissue piece, a dehydrating agent tank, an intermediate agent tank, and an admixture tank which are connected communicatably to the treatment tank, and a detection sensor to detect that a predetermined amount of liquid chemical has been transferred to the treatment tank, the method including the processes of: (a) depressurizing an inside of the treatment tank in a state that the treatment tank and the dehydrating agent tank communicate with each other and transferring a dehydrating agent from the dehydrating agent tank to the treatment tank until the dehydrating agent reaches a predetermined amount by use of the detection sensor, (b) depressurizing the inside of the treatment tank in a state that the treatment tank and the intermediate agent tank communicate with each other and transferring an intermediate agent from the intermediate agent tank to the treatment tank until the intermediate agent reaches a predetermined amount by use of the detection sensor, and (c) pressurizing the inside of the treatment tank in a state that the treatment tank and the admixture tank communicate with each other and transferring an admixture obtained by mixing the dehydrating agent and the intermediate agent supplied to the treatment tank in the respective predetermined amounts by the processes of (a) and (b) from the treatment tank to the admixture tank.

In the tissue piece treating apparatus in the one embodiment, preferably the detection sensor is provided with a plurality of liquid level sensors each to detect a liquid level of the liquid chemical transferred to the treatment tank, and each of the plurality of liquid level sensors is provided as a scale to measure the liquid chemical transferred to the treatment tank. Thereby, the treatment tank can be used as a measuring container of a liquid chemical.

Further, in the tissue piece treating apparatus in the one embodiment, preferably the plurality of liquid level sensors includes a guarantee sensor to guarantee an amount by which an amount of the liquid chemical transferred to the treatment tank immerses the tissue piece, and an upper limit sensor to prevent the liquid chemical transferred to the treatment tank from overflowing. Thereby, the liquid level sensor can be used as the guarantee sensor or the upper limit sensor.

In the tissue piece treating apparatus in the one embodiment, preferably, the plurality of processes includes the processes of: (d) after the processes of (a) to (c), immersing the tissue piece into the dehydrating agent in the treatment tank; (e) after the process of (d), immersing the tissue piece into the admixture in the treatment tank; (f) after the process of (e), immersing the tissue piece into the dehydrating agent in the treatment tank; (g) after the process of (f), immersing the tissue piece into the intermediate agent in the treatment tank; and (h) after the process of (g), immersing the tissue piece into an embedding agent in the treatment tank. Thereby, it is possible to obtain a sample for which the degreasing has been performed sufficiently.

Advantageous Effects of Invention

Briefly explaining an advantageous effect obtained by representative one of inventions disclosed in the present application, it is possible to prepare a mixed liquid having a certain ratio in a tissue piece treating apparatus.

DESCRIPTION OF EMBODIMENTS

While the following embodiment of the present invention will be explained divided into a plurality of sections or the like as needed, in principle, the plurality of sections is not unrelated with one another, but one section has a relationship as a variation example, details, or the like of a part of or the whole of another section. Accordingly, in all the drawings, the same sign is attached to a member having the same function, and the repeated explanation thereof will be omitted.

Further, a number of constituent elements (including the number of pieces, a numerical value, an amount, a range, and the like) is not limited to a specific number and may be not smaller or not larger than the specific number, except a case explicitly mentioned in particular, a case limited to a specific number theoretically, or the like. Further, when the shape of a constituent element or the like is mentioned, the shape includes a shape or the like substantially approximate or similar to the shape, or the like, except a case explicitly mentioned in particular, a case considered apparently otherwise theoretically, or the like.

Figure 1:
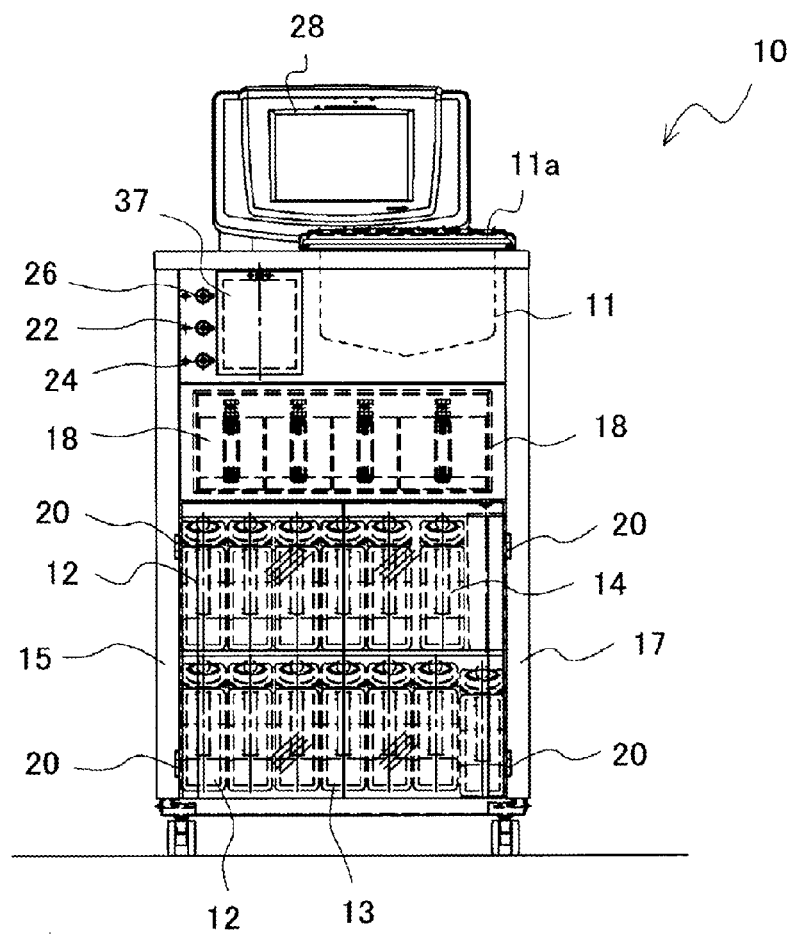
FIG. 1 is a front view of a tissue piece treating apparatus in one embodiment of the present invention.
Figure 2:
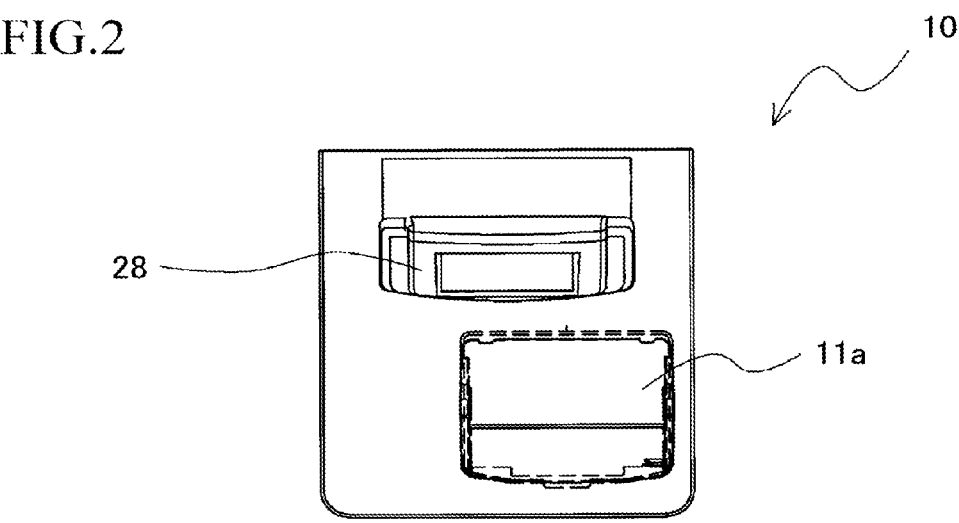
FIG. 2 is a top view of the tissue piece treating apparatus shown in FIG. 1.
Figure 3:
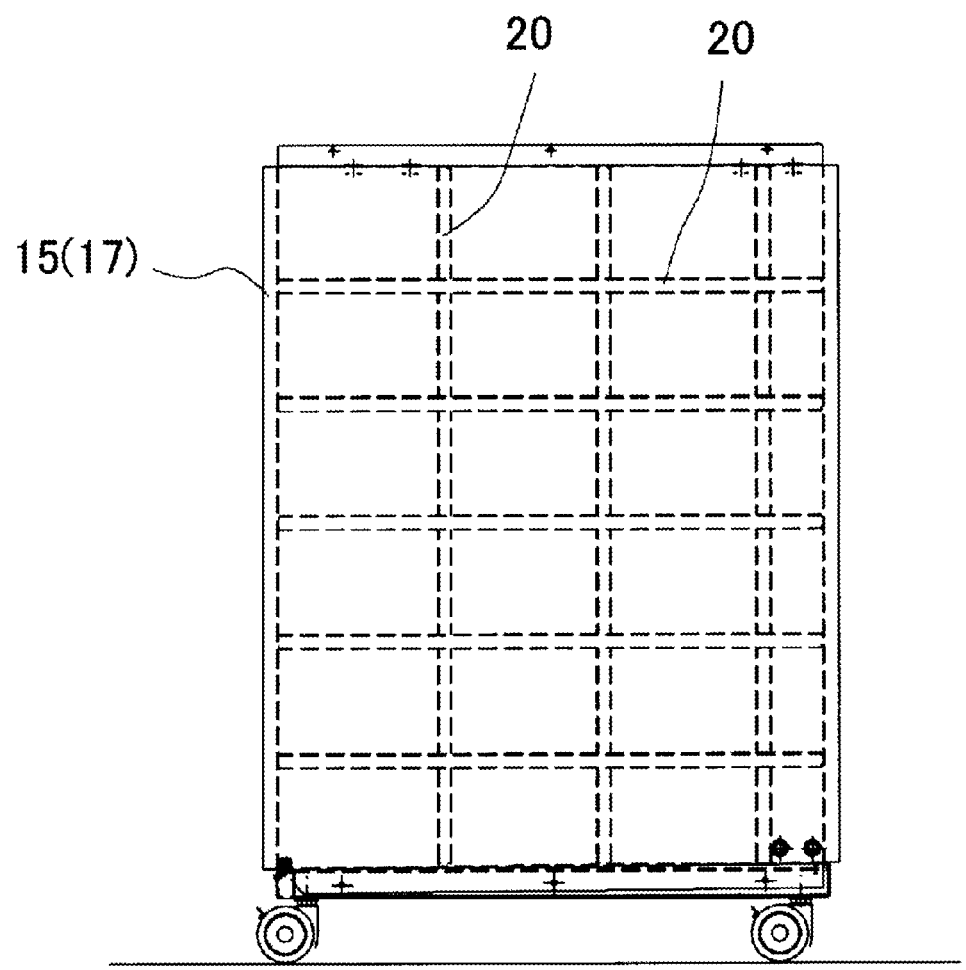
FIG. 3 is a side view of the tissue piece treating apparatus shown in FIG. 1.
Figure 4:
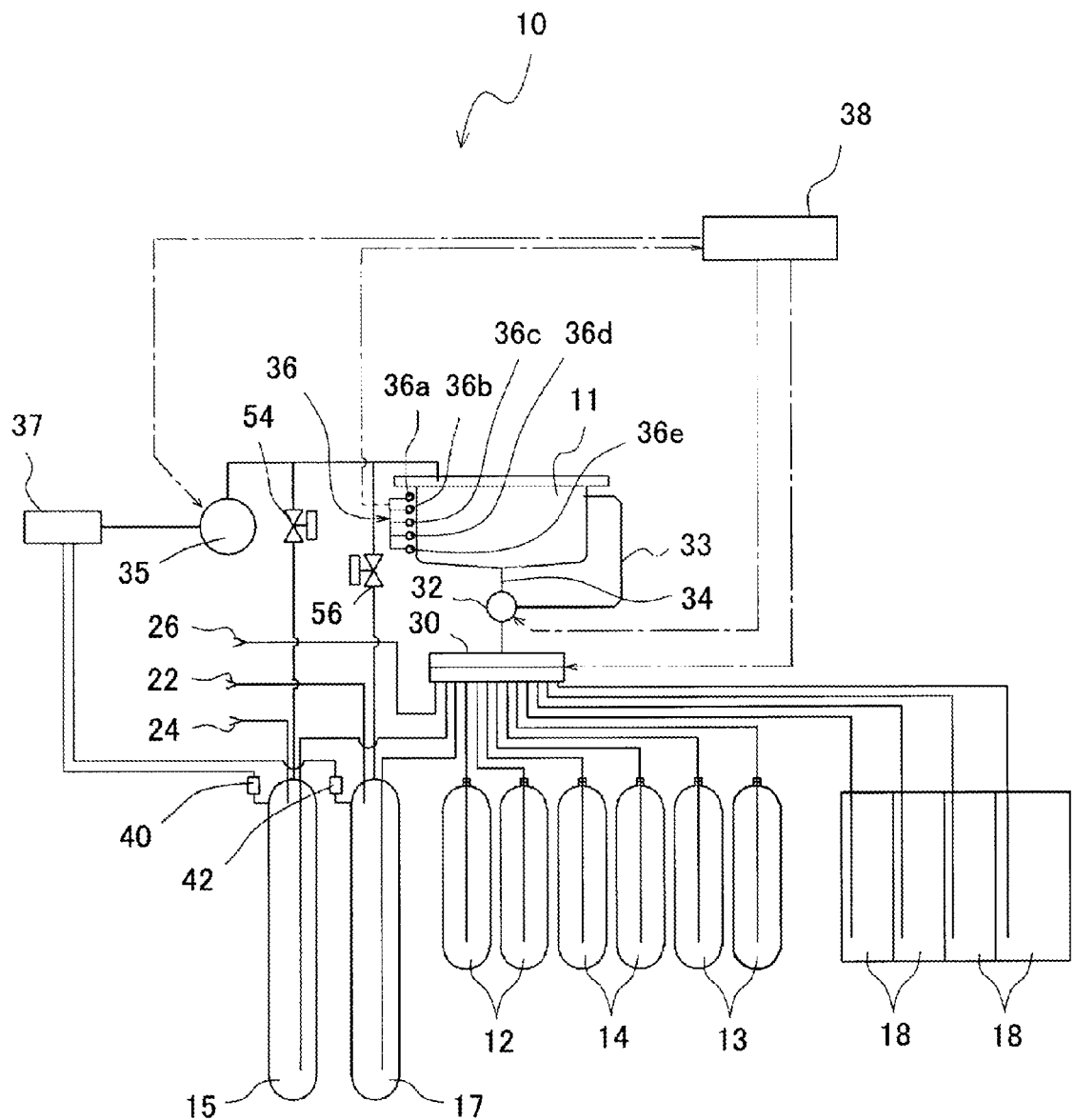
FIG. 4 is a system diagram of the tissue piece treating apparatus shown in FIG. 1.

First, there will be explained a configuration of a tissue piece treating apparatus in an embodiment of the present invention with reference to FIG. 1 to FIG. 4. FIG. 1 to FIG. 4 are a front view, a top view, a side view, and a system diagram of a tissue piece treating apparatus 10, respectively. Note that each of FIG. 1 to FIG. 3 shows a constituent member seen through the inside of the apparatus with a broken line.

The tissue piece treating apparatus 10 is provided with a monitor 28 provided on the top of the apparatus main body. This monitor 28 can display a treatment applied to a tissue piece, and the like.

Further, the tissue piece treating apparatus 10 is provided with a treatment tank 11 (also called a retort) and a cover 11a which opens or closes the treatment tank 11. For example, in the state that the tissue piece is contained in a basket (not shown in the drawing), the cover 11a of the treatment tank 11 is opened and the tissue piece is put into or taken from the treatment tank 11. Then, the cover 11a of the treatment tank 11 is closed and a liquid chemical treatment (immersion treatment) is performed for the tissue piece contained in the treatment tank 11.

Further, the tissue piece treating apparatus 10 is provided with a plurality of liquid chemical tanks which is communicatably connected to the treatment tank 11 and stores various kinds of liquid chemical to be used in a treatment of the tissue piece. The various kinds of liquid chemical include ethanol (dehydrating agent), xylene (intermediate agent), xylene-ethanol mixed liquid (admixture) which mixes ethanol and xylene, and paraffin (embedding agent), for example. Further, the plurality of liquid chemical tanks includes a dehydrating agent tank 12, an intermediate agent tank 13, an admixture tank 14, large-capacity tanks 15 and 17 each of which has a larger capacity than the dehydrating agent tank 12 and the intermediate agent tank 13 (e.g., approximately 2 to 3 times), and an embedding agent tank 18, for storing these liquid chemicals. The large-capacity tanks 15 and 17 store unused liquid chemicals (also called new liquids). This large-capacity tank 15 is used as a dehydrating agent tank, and the large-capacity tank 17 is used as an intermediate agent tank.

Upper, middle, and lower liquid chemical tank shelves are provided inside the apparatus. Arranged on the middle and lower shelves, a plurality of dehydrating agent tanks 12, a plurality of intermediate agent tanks 13, and a plurality of admixture tanks 14 are provided as internal tanks. Note that it is also possible to provide a reserve tank storing a liquid chemical which becomes unable to apply a treatment to a tissue piece, or storing any of the liquid chemicals as a reserve liquid chemical on these middle and lower shelves.

Further, arranged on the upper shelf inside the apparatus, the embedding agent tank 18 is provided as an internal tank. Since a tissue piece is immersed into melted paraffin in the embedding treatment and the paraffin is solidified at a room temperature, the upper shelf is configured as a 60° C. oven, for example, to keep the paraffin in a melted state. Note that a heater (not shown in the drawing) is provided on an outer side face in the bottom part of the treatment tank 11 for keeping the paraffin in the melted state and for keeping the temperature of each liquid chemical at a predetermined temperature during an immersion treatment.

Further, each of the large-capacity tanks 15 and 17 has a capacity approximately two to three times larger than the dehydrating agent tank 12 and the intermediate agent tank 13, and is formed in a thin plate shape for achieving a compact size of the tissue piece treating apparatus 10. These large-capacity tanks 15 and 17 are integrally attached to both side wall surfaces of the apparatus main body for securing a structural strength of the tissue piece treating apparatus 10. Then, in the large-capacity tanks 15 and 17, a plurality of reinforcement members 20 is jointed to each inner wall surface in a parallel-cross shape for reinforcement (refer to FIG. 3). By using the reinforcement members 20 in a parallel-cross shape, it is possible to make distortion of the large-capacity tank 15 or 17 as small as possible even if the inside of the tank is depressurized when a new liquid is transferred to the large-capacity tank 15 or 17 from the outside of the apparatus, or even if the inside of the tank is pressurized by storing a predetermined amount of liquid chemical.

Further, there is a possibility that the liquid chemical in the large-capacity tank 15 or 17 is evaporated by an external temperature and the inner pressure of the large-capacity tank 15 or 17 is increased. Accordingly, for preventing the pressure in the tank from being increased to a specified value or more by the evaporated gas, the tissue piece treating apparatus 10 includes a safety valve 40 provided for the large-capacity tank 15 and a safety valve 42 provided for the large-capacity tank 17 (refer to FIG. 4). Then, the tissue piece treating apparatus 10 includes a filter 37 (e.g., activated carbon filter) provided easily replaceably on the front face of the apparatus for removing stink of the gas evaporated from the safety valves 40 and 42 (refer to FIG. 1 and FIG. 4).

Further, the tissue piece treating apparatus 10 includes supply ports 22 and 24 to supply new liquids to the large-capacity tanks 15 and 17, and a supply/drain port 26 to supply/drain a liquid chemical to/from the treatment tank 11, which are provided on the front face of the apparatus main body. The supply ports 22 and 24 and the supply/drain port 26 are connected to detachable external tanks (liquid chemical tanks) provided outside the tissue piece treating apparatus 10 via a liquid chemical pipe line. An unused liquid chemical is transferred (supplied) to the large-capacity tank 15 from an external tank (new liquid tank) via the supply port 22. Further, an unused liquid chemical is transferred (supplied) to the large-capacity tank 17 from an external tank (new liquid tank) via the supply port 24. Further, an unused liquid chemical is transferred (supplied) to the treatment tank 11 from an external tank (new liquid tank) via the supply/drain port 26, and a used liquid chemical (wasted liquid) is transferred (drained) from the treatment tank 11 to an external tank (wasted liquid tank) via the supply/drain port 26.

Further, the tissue piece treating apparatus 10 is provided with a selection valve 30 (e.g., rotary valve driven by an electric motor) connected to the treatment tank 11 via a liquid chemical pipe line on one side and connected to each of the plurality of liquid chemical tanks via a liquid chemical pipe line on the other side. This selection valve 30 enables a liquid chemical tank selected from the dehydrating agent tank 12, the intermediate agent tank 13, the admixture tank 14, the large-capacity tanks 15 and 17, the embedding agent tank 18, and the external tanks (new liquid tanks and wasted liquid tank) connected to the supply/drain port 26 to communicate with the treatment tank 11.

Further, the tissue piece treating apparatus 10 includes a switch valve 32 (electromagnetic type) provided at a middle point of the liquid chemical pipe line connecting the treatment tank 11 and the selection valve 30. The switch valve 32 is a three-way valve, and connected to, other than the selection valve 30, the upper part of the treatment tank via a liquid chemical pipe line 33 and connected to the bottom part of the treatment tank 11 via a liquid chemical pipe line 34. The switch valve 32, when a liquid chemical is supplied (transferred) to the treatment tank 11, sets the liquid chemical pipe line 33 into an open state and the liquid chemical pipe line 34 into a closed state to cause the treatment tank 11 and the selection valve 30 to communicate with each other. Further, the switch valve 32, when a liquid chemical is drained (transferred) from the treatment tank 11, sets the liquid chemical pipe line 33 into a closed state and the liquid chemical pipe line 34 into an open state to cause the treatment tank 11 and the selection valve 30 to communicate with each other. Further, the switch valve 32, when a tissue is immersed into a liquid chemical in the treatment tank 11, sets the liquid chemical pipe line 33 into the closed state and the liquid chemical pipe line 34 into the closed state to disconnect the treatment tank 11 from the selection valve 30.

Further, the tissue piece treating apparatus 10 includes a pump 35 which is connected to the upper part of the treatment tank 11 (higher part than a liquid level sensor 36*a* to be described below) via an air pipe line and depressurizes or pressurizes the inside of the treatment tank 11, and the filter 37 which is connected to the pump 35 via an air pipe line. This pump 35 performs suction of air and exhaustion of liquid chemical mixed gas in the treatment tank 11 via the filter 37. The pump 35 is used for depressurizing (sucking air from) the inside of the treatment tank 11 when transferring (pulling in) a liquid chemical from a selected liquid chemical tank to the treatment tank 11. Further, the pump 35 is used for pressurizing (ejecting air into) the inside of the treatment tank 11 when transferring (sending out) a liquid chemical from the treatment tank 11 to a selected liquid chemical tank.

An air pipe line (equalizing line) from the large-capacity tank 15 and an air pipe line (equalizing line) from the large-capacity tank 17 are provided at middle points of the air line connected to this pump 35. Then, the tissue piece treating apparatus 10 includes open/close valves 54 and 56 provided for these respective air pipe lines. These open/close valves 54 and 56 may be manual types or electromagnetic types. The open/close valves 54 and 56 are set to open states only when the liquid chemicals in the external tanks are supplied (including replenishment) to the large-capacity tanks 15 and 17 via the supply ports 22 and 24, and set to closed states during the other processes, respectively.

Further, the tissue piece treating apparatus 10 includes a detection sensor 36 to detect that a liquid chemical has been transferred to the treatment tank 11 in a predetermined amount. This detection sensor 36 includes a plurality of liquid level sensors 36*a*, 36*b*, 36*c*, 36*d*, and 36*e* provided as scales to measure a liquid chemical transferred to the treatment tank 11. By providing the plurality of liquid level sensors 36*a* to 36*e* for the treatment tank 11 in this manner, it is possible to use the treatment tank 11 as a measuring container. For example, the plurality of liquid level sensors 36*a* to 36*e* is provided so as to cause the liquid amount between the bottom of the treatment tank 11 and the liquid level sensor 36*e*, the liquid amount between the liquid level sensor 36*e* and the liquid level sensor 36*d*, the liquid amount between the liquid level sensor 36*d* and the liquid level sensor 36*c*, the liquid amount between the liquid level sensor 36*c* and the liquid level sensor 36*b*, and the liquid amount between the liquid level sensor 36*b* and the liquid level sensor 36*a* to be the same. Note that, by providing more liquid level sensors, it is possible to make the scales finer in the treatment tank 11.

Then, the liquid level sensor 36*a* is also used an upper limit sensor to prevent a liquid chemical transferred to the treatment tank 11 from overflowing. Further, the liquid level sensor 36*c* is also used as a guarantee sensor to guarantee an amount by which an amount of liquid chemical transferred to the treatment tank 11 immerses a tissue piece.

Further, the tissue piece treating apparatus 10 includes a control unit 38 which is connected electrically to the selection valve 30, the switch valve 32, the pump 35, and the detection sensor 36 via respective wirings, and carries out a plurality of processes. The control unit 38 is configured using an arithmetic processing unit (CPU) and a storage unit (memory) and operated according to a preliminarily recorded operation program, and controls the selection valve 30 and the like by transmitting signals to drive the selection valve 30, the switch valve 32, and the pump 35, receiving a detection signal from the detection sensor 36, and the like. Note that control data such as process operation start instruction and process data for each process are input into the control unit 38 by an operation unit (not shown in the drawing).

Figure 5:
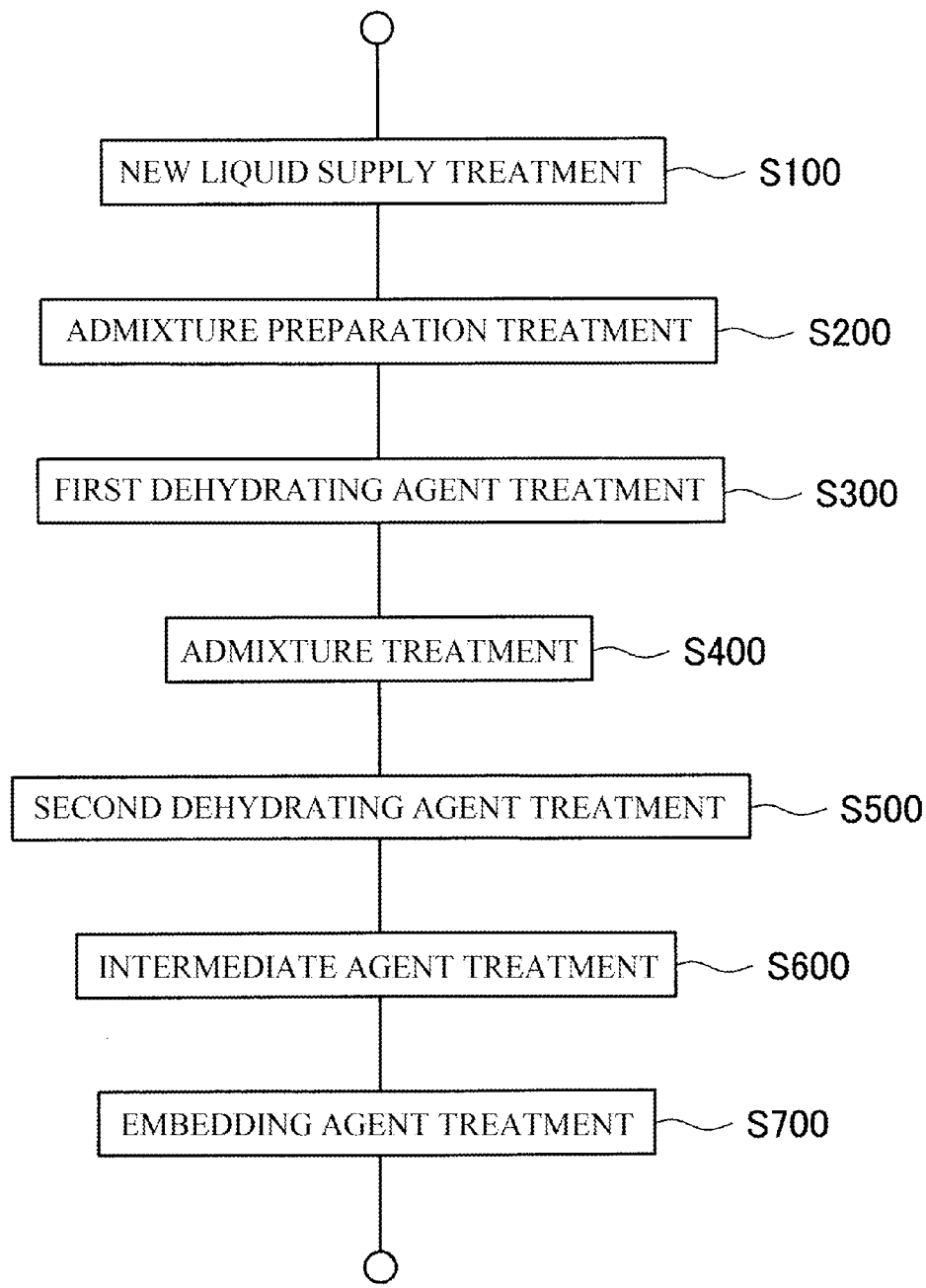
FIG. 5 is a process flowchart of a sample preparation method in one embodiment of the present invention.
Figure 6:
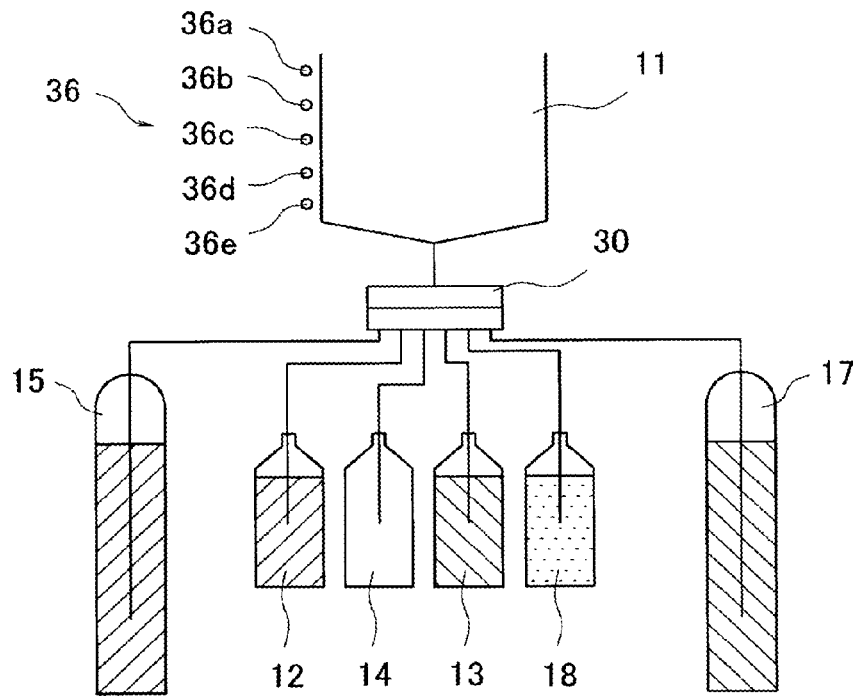
FIG. 6 is an explanatory diagram for explaining a mixed liquid preparation process in one embodiment of the present invention.

Next, there will be explained a sample preparation method using the tissue piece treating apparatus in the embodiment of the present invention with reference to FIG. 4 to FIG. 9. FIG. 5 is a process flowchart of the sample preparation method, and a part thereof overlaps with a process flow of the control unit 38. Further, FIG. 6 to FIG. 9 are explanatory diagrams for explaining a preparation process of the mixed liquid. Note that, in FIG. 6 to FIG. 9, a relevant part of the tissue piece treating apparatus is shown in a simplified manner for clear explanation.

First, a new liquid is supplied to (stored into) a liquid chemical tank of the tissue piece treating apparatus 10 (step S100 of FIG. 5). Specifically, ethanol is supplied to the dehydrating agent tank 12, xylene is supplied to the intermediate agent tank 13, and paraffin is supplied to the embedding agent tank 18 (refer to FIG. 6). Further, ethanol is supplied to the large-capacity tank 15, and xylene is supplied to the large-capacity tank 17.

Subsequently, a mixed liquid (liquid chemical) is prepared inside the apparatus, and the mixed liquid is transferred (supplied) to the admixture tank 14 of a liquid chemical tank in the tissue piece treating apparatus 10 (step S200 of FIG. 5).

Figure 7:
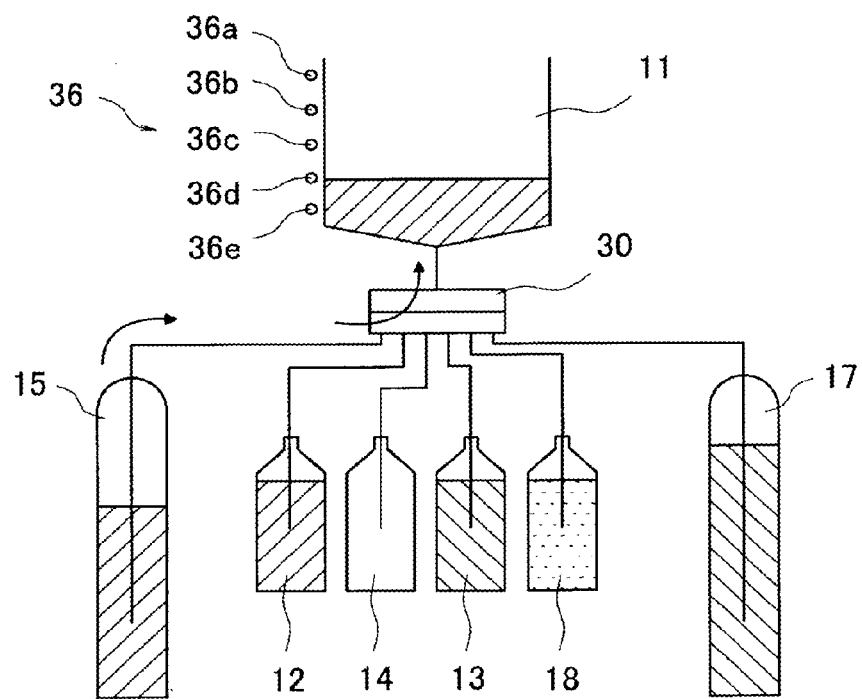
FIG. 7 is an explanatory diagram for explaining a mixed liquid preparation process succeeding FIG. 6.

First, the selection of the selection valve 30 and the switching of the switch valve 32 are performed so as to cause the large-capacity tank 15 and the treatment tank 11 to communicate with each other, and the inside of the treatment tank 11 is depressurized by the pump 35 and the ethanol in the large-capacity tank 15 is sucked to be transferred into the treatment tank 11 (refer to FIG. 7). At this time, the ethanol is transferred from the large-capacity tank 15 (dehydrating agent tank) to the treatment tank 11 until reaching a predetermined amount by use of the detection sensor 36, that is, until the detection of the liquid level sensor 36*d*.

Figure 8:
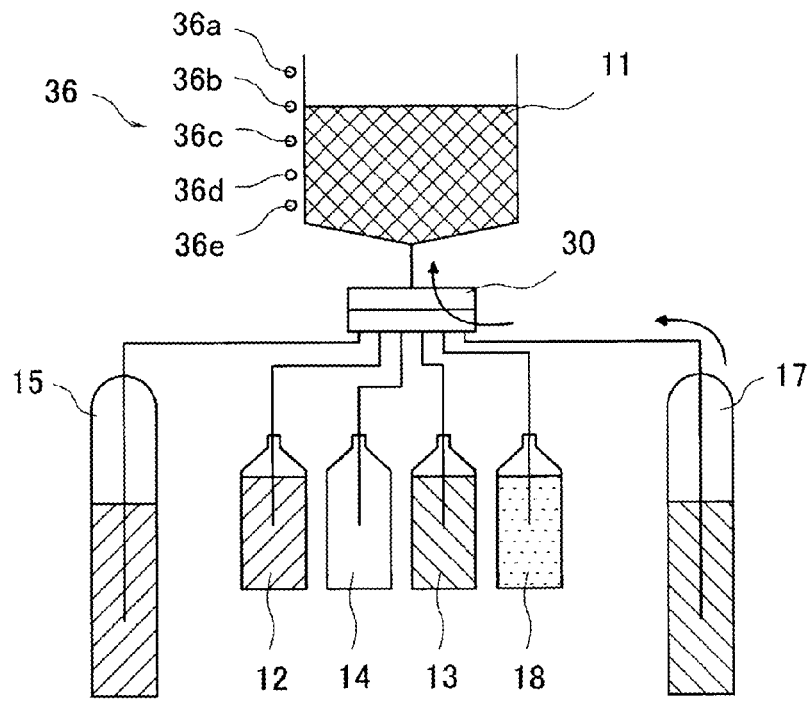
FIG. 8 is an explanatory diagram for explaining a mixed liquid preparation process succeeding FIG. 7.

Subsequently, the selection of the selection valve 30 and the switching of the switch valve 32 are performed so as to cause the large-capacity tank 17 and the treatment tank 11 to communicate with each other, and the inside of the treatment tank 11 is depressurized by the pump 35 and the xylene in the large-capacity tank 17 is sucked to be transferred into the treatment tank 11 (refer to FIG. 8). At this time, the xylene is transferred from the large-capacity tank 17 (intermediate agent tank) to the treatment tank 11 until reaching a predetermined amount by use of the detection sensor 36, that is, until the detection of the liquid level sensor 36*b*. Thereby, the ethanol transferred into the treatment tank 11 previously and the xylene are mixed at a ratio (mixing ratio) of 1:1 and a xylene-ethanol mixed liquid is prepared.

Here, the ratio of the ethanol and the xylene is not limited to 1:1, and can be changed variously by an input setting of a worker (e.g., selection from a selection screen of the monitor 28). For example, when the ratio of the ethanol and the xylene is set to 1:2, after the ethanol is transferred to the treatment tank 11 until the detection of the liquid level sensor 36*e*, the xylene may be transferred further to the treatment tank 11 until the detection of the liquid level sensor 36*c*. When the xylene-ethanol mixed liquid is to be prepared in a finer ratio, more liquid level sensors may be provided as scales to measure a liquid chemical transferred to the treatment tank 11.

Figure 9:
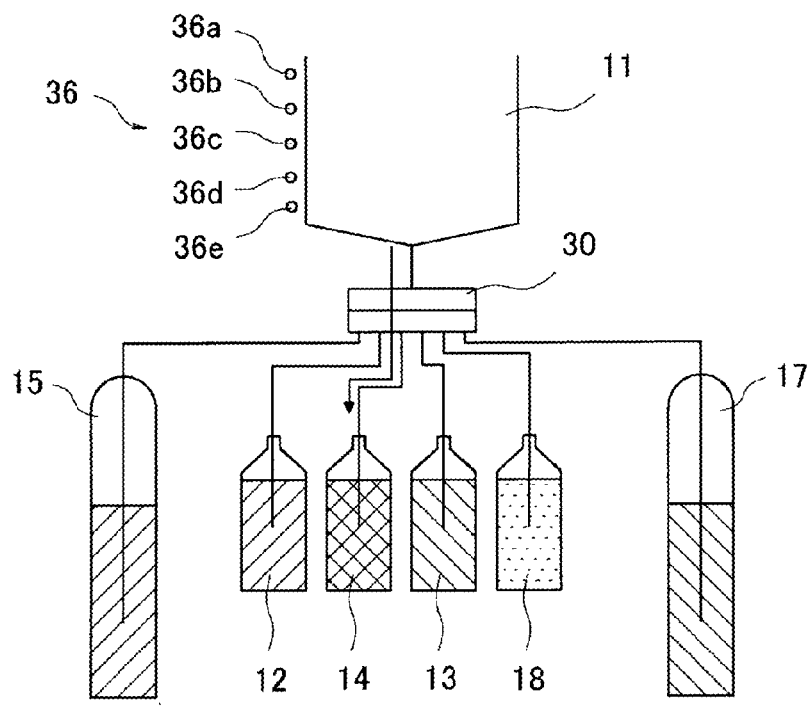
FIG. 9 is an explanatory diagram for explaining a mixed liquid preparation process succeeding FIG. 8.

Next, the selection of the selection valve 30 and the switching of the switch valve 32 are performed so as to cause the treatment tank 11 and the admixture tank 14 of a transfer destination to communicate with each other, the inside of the treatment tank 11 is pressurized by the pump 35, and the xylene-ethanol mixed liquid in the treatment tank 11 is compressed to be transferred to the admixture tank 14 of the transfer destination (refer to FIG. 9).

In this manner, by using the detection sensor 36 to detect that a predetermined amount of liquid chemical has been transferred to the treatment tank 11, it is possible to automatically prepare a mixed liquid having a certain ratio in the tissue piece treating apparatus 10. Further, only by input setting of the worker, it is possible to easily prepare the mixed liquid having a certain ratio automatically. Further, since the mixed liquid is prepared inside the tissue piece treating apparatus 10 provided with the filter 37, it is possible to keep the room environment healthy.

Subsequently, a first dehydrating agent treatment is performed by ethanol immersing (step S300 of FIG. 5). In advance to this treatment, a tissue piece is put into a basket (not shown in the drawing) and the basket is contained in the treatment tank 11. Here, as liquid chemical tanks (internal tanks) of the tissue piece treating apparatus 10, three dehydrating agent tanks 12 (in the following, signs 12a, 12b, and 12c are attached) are assumed to be secured for storing ethanol. Note that the number of dehydrating agent tanks 12 to be secured can be changed by the setting of the worker.

First, the selection of the selection valve 30 and the switching of the switch valve 32 are performed so as to cause the dehydrating agent tank 12a and the treatment tank 11 to communicate with each other, and the inside of the treatment tank 11 is depressurized by the pump 35 and the ethanol in the dehydrating agent tank 12a is sucked to be transferred into the treatment tank 11.

At this time, the ethanol is transferred from the dehydrating agent tank 12a to the treatment tank 11 until reaching a predetermined amount by use of the detection sensor 36, that is, until the detection of the liquid level sensor 36c which serves as the guarantee sensor. That is, the liquid surface of the ethanol transferred into the treatment tank 11 exists between the liquid level guarantee sensor 36c and the upper limit sensor 36a, and the amount of the ethanol is an amount capable of immersing the tissue piece sufficiently in the ethanol. When the liquid level sensor 36c cannot detect the ethanol, the ethanol can be replenished from the large-capacity tank 15 or the dehydrating agent tank 12b to the treatment tank 11. Note that it is also possible to transfer (replenish) another liquid chemical such as xylene in a similar manner using the detection sensor 36.

Next, after the tissue piece has been immersed in the ethanol for a predetermined time, the selection of the selection valve 30 and the switching of the switch valve 32 are performed so as to cause the treatment tank 11 and the dehydrating agent tank 12a to communicate with each other, and the inside of the treatment tank 11 is pressurized by the pump 35 and the ethanol in the treatment tank 11 is compressed to be transferred to the dehydrating agent tank 12a.

Similarly, the tissue piece is immersed in order into the ethanol transferred from each of the dehydrating agent tanks 12b and 12c to the treatment tank 11. By the first dehydrating agent treatment like this, it is possible to remove the water content contained in the tissue piece to some extent.

Here, when ethanol contacts the tissue piece predetermined times, the water content or the like in the tissue piece is mixed into the ethanol and the concentration of the ethanol stored in the dehydrating agent tanks 12a, 12b, and 12c decreases. Specifically, the concentration is lowest in the ethanol of the dehydrating agent tank 12a which is used first for the treatment, and then lower in the ethanol of the dehydrating agent tank 12b and the ethanol of the dehydrating agent tank 12c in this order. Accordingly, after the first dehydrating agent treatment has been performed the predetermined times, a liquid drop treatment is performed. First, after the immersion treatment using the ethanol in the dehydrating agent tank 12a, an external tank (wasted liquid tank) connected to the supply/drain port 26 is selected by the selection valve 30 and the ethanol is drained (transferred) to the external tank from the treatment tank 11. Next, after the immersion treatment using the ethanol in the dehydrating agent tank 12b, the empty dehydrating agent tank 12a is selected by the selection valve 30 and the ethanol is transferred from the treatment tank 11 to the dehydrating agent tank 12a. Next, after the immersion treatment using the ethanol in the dehydrating agent tank 12c, the empty dehydrating agent tank 12b is selected by the selection valve 30 and the ethanol is transferred from the treatment tank 11 to the dehydrating agent tank 12b. Then, after unused ethanol in the large-capacity tank 15 is transferred to the treatment tank 11, the empty dehydrating agent tank 12c is selected by the selection valve 30 and the ethanol is supplied (transferred) from the treatment tank 11 to the dehydrating agent tank 12c. Note that the liquid drop treatment is performed similarly on another liquid chemical such as xylene.

Subsequently, a mixed liquid treatment (affinity imparting treatment) is performed by immersing the tissue piece into a xylene-ethanol mixed liquid (step S400 of FIG. 5). Here, two admixture tanks 14 (in the following, signs 14a and 14b are attached) are assumed to be secured for storing the xylene-ethanol mixed liquid, as liquid chemical tanks (internal tanks) of the tissue piece treating apparatus 10. Note that the number of the admixture tanks 14 to be secured can be changed by the setting of the worker.

First, the selection of the selection valve 30 and the switching of the switch valve 32 are performed so as to cause the admixture tank 14a and the treatment tank 11 to communicate with each other, and the inside of the treatment tank 11 is depressurized by the pump 35 and the xylene-ethanol mixed liquid in the admixture tank 14a is sucked to be transferred into the treatment tank 11.

Next, after the tissue piece has been immersed in the xylene-ethanol mixed liquid for a predetermined time, the selection of the selection valve 30 and the switching of the switch valve 32 are performed so as to cause the treatment tank 11 and the admixture tank 14a to communicate with each other, and the inside of the treatment tank 11 is pressurized by the pump 35 and the xylene-ethanol mixed liquid in the treatment tank 11 is compressed to be transferred to the admixture tank 14a.

Similarly, the tissue piece is immersed in order into the xylene-ethanol transferred from the admixture tank 14b to the treatment tank 11. By the admixture treatment like this, it is possible to cause the liquid chemical to penetrate into a deep part of the tissue piece by the synergistic effect of the grease dissolution (affinity improvement) and the dilution dehydration caused by the xylene-ethanol.

Subsequently, a second dehydrating agent treatment is performed by immersing the tissue piece into ethanol (step S500 of FIG. 5). Here, two dehydrating agent tanks 12 (in the following, signs 12d and 12e are attached) are assumed to be secured for storing the ethanol as liquid chemical tanks (internal tanks) of the tissue piece treating apparatus 10. Note that the number of dehydrating agent tanks 12 to be secured can be changed by the setting of the worker.

First, the selection of the selection valve 30 and the switching of the switch valve 32 are performed so as to cause the dehydrating agent tank 12d and the treatment tank 11 to communicate with each other, and the inside of the treatment tank 11 is depressurized by the pump 35 and the ethanol in the dehydrating agent tank 12d is sucked to be transferred into the treatment tank 11.

Next, after the tissue piece has been immersed in the ethanol for a predetermined time, the selection of the selection valve 30 and the switching of the switch valve 32 are performed so as to cause the treatment tank 11 and the dehydrating agent tank 12d to communicate with each other, and the inside of the treatment tank 11 is pressurized by the pump 35 and the ethanol in the treatment tank 11 is compressed to be transferred to the dehydrating agent tank 12d.

Similarly, the tissue piece is immersed in order into the ethanol transferred from the dehydrating agent tank 12e to the treatment tank 11. By the second dehydrating agent treatment like this, it is possible to perform further dilution dehydration by replacing the xylene-ethanol mixed liquid with the ethanol.

Subsequently, an intermediate agent treatment is performed by immersing the tissue piece into xylene (step S600 of FIG. 5). Here, three intermediate agent tanks 13 (in the following, signs 13a, 13b, and 13c are attached) are assumed to be secured for storing the xylene as liquid chemical tanks (internal tanks) of the tissue piece treating apparatus 10. Note that the number of intermediate agent tanks 13 to be secured can be changed by the setting of the worker.

First, the selection of the selection valve 30 and the switching of the switch valve 32 are performed so as to cause the intermediate agent tank 13a and the treatment tank 11 to communicate with each other, and the inside of the treatment tank 11 is depressurized by the pump 35 and the xylene in the intermediate agent tank 13a is sucked to be transferred into the treatment tank 11.

Next, after the tissue piece has been immersed in the xylene for a predetermined time, the selection of the selection valve 30 and the switching of the switch valve 32 are performed so as to cause the treatment tank 11 and the intermediate agent tank 13a to communicate with each other, and the inside of the treatment tank 11 is pressurized by the pump 35 and the xylene in the treatment tank 11 is compressed to be transferred to the intermediate agent tank 13a.

Similarly, the tissue piece is immersed in order into the xylene transferred from each of the intermediate agent tanks 13b and 13c to the treatment tank 11. By the intermediate agent treatment like this, it is possible to cause the liquid chemical to penetrate into a deep part of the tissue piece while dissolving grease in the sufficiently dehydrated tissue piece.

Subsequently, an embedding treatment is performed by immersing the tissue piece into paraffin (step S700 of FIG. 5). Here, four embedding agent tanks 18 (in the following, signs 18a, 18b, 18c, and 18d are attached) are assumed to be secured for storing the paraffin as liquid chemical tanks (internal tanks) of the tissue piece treating apparatus 10. Note that the number of the embedding agent tanks 18 to be secured can be changed by the setting of the worker.

First, the selection of the selection valve 30 and the switching of the switch valve 32 are performed so as to cause the embedding agent tank 18a and the treatment tank 11 to communicate with each other, and the inside of the treatment tank 11 is depressurized by the pump 35 and the paraffin in the embedding agent tank 18a is sucked to be transferred into the treatment tank 11.

Next, after the tissue piece has been immersed in the paraffin for a predetermined time, the selection of the selection valve 30 and the switching of the switch valve 32 are performed so as to cause the treatment tank 11 and the embedding agent tank 18a to communicate with each other, and the inside of the treatment tank 11 is pressurized by the pump 35 and the paraffin in the treatment tank 11 is compressed to be transferred to the embedding agent tank 18a.

Similarly, the tissue piece is immersed in order into the paraffin transferred from each of the embedding agent tanks 18b, 18c, and 18d to the treatment tank 11. By the embedding agent treatment like this, it is possible to cause the paraffin to penetrate into a deep part of the tissue piece where the xylene has penetrated, while dissolving grease.

According to the tissue piece treating apparatus 10 in the present embodiment, it is possible to obtain a sample (tissue piece) which enables microscope observation to be performed and is subjected to sufficient degreasing.

As above, while the present invention has been explained specifically according to the embodiment, obviously the present invention is not limited to the above embodiment and can be modified variously in a range without departing from the gist thereof.

For example, the embodiment explains the case of simplifying the configuration of the tissue piece treating apparatus 10 using the plurality of liquid level sensors 36a to 36e as the scales of the treatment tank 11 for the detection sensor 36. Not limited to this case, it is possible to detect the amount of liquid chemical transferred to the treatment tank also by using a flow rate sensor provided at the liquid chemical pipe line on the front side of the treatment tank 11.

Further, for example, while the embodiment explains the case of using ethanol as the dehydrating agent, it is also possible to use alcohol such as methanol, butanol, isopropanol, and industrial use methyl alcohol. Further, while the embodiment explains the case of using xylene as the intermediate agent, it is also possible to use a liquid chemical containing toluene, chloroform, alkane-based aliphatic hydrocarbon, or the like as a main component. Accordingly, while the embodiment explains the case of using xylene-ethanol mixed liquid as the admixture, it is also possible to use xylene-methanol mixed liquid, for example.

Further, for example, the embodiment explains the case of automatically preparing the mixed liquid having a certain ratio by providing the large-capacity tanks 15 and 17 having larger capacities than the dehydrating agent tanks 12 and the intermediate agent tank 13 and supplying the liquid from each of the tanks to the treatment tank 11. Not limited to this case, when, without the use of the large-capacity tanks 15 and 17, any of the plurality of dehydrating agent tanks 12 is used as a new liquid tank and any of the plurality of intermediate agent tanks 13 is used as a new liquid tank, and thereby the mixed liquid having a certain ratio also can be prepared automatically.

Further, for example, while the embodiment explains the case of supplying ethanol first to the treatment tank 11 and then supplying xylene further to the treatment tank 11 when the xylem-ethanol mixed liquid is prepared, the xylene may be supplied first to the treatment tank 11 and then the ethanol may be supplied further to the treatment tank 11.

Further, for example, the embodiment explains the case of using ethanol as the dehydrating agent and xylene as the intermediate agent, and preparing the xylem-ethanol mixed liquid from the dehydrating agent and intermediate agent tanks. Not limited to this case, when methanol is used as the dehydrating agent, xylene is used as the intermediate agent, ethanol is stored in another liquid chemical tank provided separately from the dehydrating agent tank, it is also possible to prepare the xylene-ethanol mixed liquid from the another liquid chemical tank and the intermediate agent tank.

Further, for example, while the embodiment explains the case of preparing a sample by performing the first dehydrating agent treatment, the admixture treatment, the second dehydrating agent treatment, the intermediate agent treatment, and the embedding agent treatment in this order, when the dehydration of a tissue piece is sufficiently performed by the admixture treatment, it is also possible to omit the second dehydrating agent treatment.

What is claimed is:

1. A tissue piece treating apparatus, comprising:
a treatment tank to contain a tissue piece;
a plurality of liquid chemical tanks that is connected communicatably to said treatment tank and stores liquid chemicals;
a pump that depressurizes an inside of said treatment tank when a liquid chemical is transferred from said liquid chemical tank communicating with said treatment tank to said treatment tank, and pressurizes the inside of said treatment tank when a liquid chemical is transferred from said treatment tank to said liquid chemical tank communicating with the treatment tank;
a detection sensor to detect that a predetermined amount of liquid chemical has been transferred to said treatment tank; and
a control unit that is connected to said pump and said detection sensor via respective wirings and carries out a plurality of processes,
said plurality of processes including the processes of
(a) transferring a dehydrating agent from said liquid chemical tank storing said dehydrating agent to said treatment tank until said dehydrating agent reaches a predetermined amount by use of said detection sensor,
(b) transferring an intermediate agent from said liquid chemical tank storing said intermediate agent to said treatment tank until said intermediate agent reaches a predetermined amount by use of said detection sensor, and
(c) transferring an admixture obtained by mixing said dehydrating agent by said process (a) and said intermediate agent by said process (b) from said treatment tank to said liquid chemical tank in which said admixture is stored.

2. The tissue piece treating apparatus according to claim 1, wherein
said detection sensor is provided with a plurality of liquid level sensors each to detect a liquid level of said liquid chemical transferred to said treatment tank, and
each of said plurality of liquid level sensors is provided as a scale to measure said liquid chemical transferred to said treatment tank.

3. The tissue piece treating apparatus according to claim 2, wherein the plurality of liquid level sensors includes an upper limit sensor to prevent said liquid chemical transferred to said treatment tank from overflowing, and a guarantee sensor to guarantee an amount by which an amount of said liquid chemical transferred to said treatment tank immerses said tissue piece.

4. The tissue piece treating apparatus according to claim 1, wherein
said plurality of processes includes the processes of:
(d) after said processes of (a) to (c), immersing said tissue piece into the dehydrating agent in said treatment tank;
(e) after said process of (d), immersing said tissue piece into the admixture in said treatment tank;
(f) after said process of (e), immersing said tissue piece into the dehydrating agent in said treatment tank;
(g) after said process of (f), immersing said tissue piece into the intermediate agent in said treatment tank; and
(h) after said process of (g), immersing said tissue piece into an embedding agent in said treatment tank.

5. A method of operating a tissue piece treating apparatus including a treatment tank to contain a tissue piece, a dehydrating agent tank, an intermediate agent tank, and an admixture tank which are connected communicatably to said treatment tank, and a detection sensor to detect that a predetermined amount of liquid chemical has been transferred to said treatment tank, the method comprising the processes of:
(a) depressurizing an inside of said treatment tank in a state that said treatment tank and said dehydrating agent tank communicate with each other and transferring a dehydrating agent from said dehydrating agent tank to said treatment tank until the dehydrating agent reaches a predetermined amount by use of said detection sensor,
(b) depressurizing the inside of said treatment tank in a state that said treatment tank and said intermediate agent tank communicate with each other and transferring an intermediate agent from said intermediate agent tank to said treatment tank until the intermediate agent reaches a predetermined amount by use of said detection sensor, and
(c) pressurizing the inside of said treatment tank in a state that said treatment tank and said admixture tank communicate with each other and transferring an admixture obtained by mixing said dehydrating agent and said intermediate agent supplied to said treatment tank in the respective predetermined amounts by said processes of (a) and (b) from said treatment tank to said admixture tank.

* * * * *